US008225666B2

(12) United States Patent
McAleavey (10) Patent No.: US 8,225,666 B2
(45) Date of Patent: Jul. 24, 2012

(54) SHEAR MODULUS ESTIMATION BY APPLICATION OF SPATIALLY MODULATED IMPULSE ACOUSTIC RADIATION FORCE APPROXIMATION (75) Inventor: Stephen McAleavey, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 12/118,359

(22) Filed: May 9, 2008

(65) Prior Publication Data
US 2009/0056453 A1 Mar. 5, 2009

Related U.S. Application Data (60) Provisional application No. 60/917,031, filed on May 9, 2007.

(51) Int. Cl.
G01N 9/24 (2006.01)
(52) U.S. Cl. ............................. 73/602; 73/645; 600/442
(58) Field of Classification Search .................... 73/597, 73/602, 645, 646, 647, 648
See application file for complete search history.

(56) References Cited

U.S. PATENT DOCUMENTS

| 4,930,111 | A | * | 5/1990 | Sullivan et al. | ............... | 367/130 |
|---|---|---|---|---|---|---|
| 5,305,091 | A | * | 4/1994 | Gelbart et al. | ............... | 356/620 |
| 5,661,816 | A | * | 8/1997 | Fantone et al. | ............... | 382/100 |
| 5,825,186 | A | * | 10/1998 | Ehman et al. | ............... | 324/309 |
| 6,008,887 | A | * | 12/1999 | Klein et al. | ............... | 356/28.5 |
| 6,561,981 | B2 | * | 5/2003 | Bonnefous | ............... | 600/443 |
| 6,770,033 | B1 | * | 8/2004 | Fink et al. | ............... | 600/443 |
| 7,107,159 | B2 | * | 9/2006 | German | ............... | 702/41 |
| 7,444,875 | B1 | * | 11/2008 | Wu et al. | ............... | 73/602 |
| 7,966,134 | B2 | * | 6/2011 | German | ............... | 702/41 |
| 2003/0204141 | A1 | * | 10/2003 | Nock et al. | ............... | 600/439 |
| 2004/0034304 | A1 | * | 2/2004 | Sumi | ............... | 600/439 |
| 2004/0068184 | A1 | * | 4/2004 | Trahey et al. | ............... | 600/437 |
| 2004/0075824 | A1 | * | 4/2004 | Belenkii et al. | ............... | 356/28 |
| 2005/0054930 | A1 | * | 3/2005 | Rickets et al. | ............... | 600/453 |
| 2005/0252295 | A1 | * | 11/2005 | Fink et al. | ............... | 73/603 |
| 2006/0173319 | A1 | * | 8/2006 | Sumi | ............... | 600/437 |
| 2006/0184020 | A1 | * | 8/2006 | Sumi | ............... | 600/437 |
| 2007/0016031 | A1 | * | 1/2007 | Mourad et al. | ............... | 600/437 |
| 2007/0060817 | A1 | * | 3/2007 | Davies | ............... | 600/437 |
| 2007/0093716 | A1 | * | 4/2007 | Radulescu | ............... | 600/437 |
| 2008/0249408 | A1 | * | 10/2008 | Palmeri et al. | ............... | 600/438 |

OTHER PUBLICATIONS

International Search Report and Written Opinion of PCT/US2008/063294; Oct. 21, 2008; University of Rochester et al.; 8 pages.

* cited by examiner

Primary Examiner — Hezron E Williams
Assistant Examiner — Samir M Shah
(74) Attorney, Agent, or Firm — Hodgson Russ LLP (57) ABSTRACT A method for determining a shear modulus of an elastic material with a known density value is provided. In this method, a spatially modulated acoustic radiation force is used to initially generate a disturbance of known spatial frequency or wavelength. The propagation of this initial displacement as a shear wave is measured using ultrasound tracking methods. A temporal frequency is determined based on the shear wave. The shear modulus of the elastic material at the point of excitation may be calculated using the values of the spatial wavelength, material density, and temporal frequency.

8 Claims, 9 Drawing Sheets

SHEAR MODULUS ESTIMATION BY APPLICATION OF SPATIALLY MODULATED IMPULSE ACOUSTIC RADIATION FORCE APPROXIMATION

REFERENCE TO RELATED APPLICATION

The present application claims the benefit of U.S. Provisional Application No. 60/917,031, filed May 9, 2007, whose disclosure is hereby incorporated by reference in its entirety into the present application.

FIELD OF THE INVENTION

The present invention relates to a method for determining a shear modulus, i.e., stiffness, of an elastic material such as human or animal soft tissues. More particularly, the method of the present invention provides an ultrasonic measurement of tissue shear modulus for the diagnosis of disease, such as liver fibrosis and prostate cancer.

DESCRIPTION OF RELATED ART

Quantification of tissue shear modulus ("stiffness") is needed for disease diagnosis, therapy monitoring, and biomechanics research. Changes in tissue stiffness have long been associated with disease or injury. Manual palpation has been used to detect these changes. Manual palpation is limited to superficial or accessible tissues. Nonetheless, manual palpation can reveal structures that may not be evident in conventional imaging modalities. For instance, prostate cancer is often invisible to ultrasound, while the stiffening of the prostate is detectable by palpation. Radio frequency (RF) and high intensity focused ultrasound (HIFU) ablation can cause tissue necrosis and stiffening of tissue, while being invisible to ultrasound.

The limitations and diagnostic utility of palpation have led to an interest in elastography, the generation of images of or related to tissue stiffness. These images are useful because disease or therapeutic processes may cause a significant change in tissue stiffness without a concomitant change in ultrasound echogenicity or x-ray density. A number of techniques have been explored including strain elastography, transient elastography, sonoelastography, vibroacoustograpy, and acoustic radiation force impulse imaging (ARFI). ARFI is attractive because of potential to induce measurable displacement wherever an ultrasound beam may penetrate. Sonoelasticity methods, both transient and steady-state have the potential to provide a quantitative estimate of shear modulus.

It is well known that the shear modulus G of a linear elastic material with density $\rho$ is related to the speed of shear wave propagation $c_s$ by $c_s = \sqrt{G/\rho}$. Many authors have used this relationship to estimate the local shear modulus of tissues. In one of these methods, a point or extended source is driven at a given frequency, and the local wavelength of the shear wave is estimated by ultrasonic or magnetic resonance imaging (MRI) measurements of the induced displacement field. A variety of techniques are employed but all depend on a source of known temporal frequency. Other methods employ step excitation to generate non-harmonic shear waves, and local shear modulus properties are estimated by inversion of the wave equation or arrival time methods. However, the inversion method is sensitive to noise.

The background theory of the present invention is as follows:

In a linear elastic material the shear component of wave motion is governed by the homogenous wave equation:

$$\rho \frac{\partial^2 u_i}{\partial t^2} - G \nabla^2 u_i = 0 \tag{1}$$

where $u_i$ is the displacement in the i direction, G is the shear modulus, and r the material density. A simple solution to this equation is the shear plane wave described by $u_z = A \cos(kx - ct)$, $u_x = u_y = 0$. Here $c = \sqrt{G/\rho}$ is the shear wave velocity and $k = w/c$ is the wavenumber. The shear modulus can be determined in a material of known density through knowledge of the frequency and wavelength of such a wave. In situations where the shear wave is artificially generated one of the wave properties may be known a priori. For instance, in "Sonoelastographic imaging of interference patterns for estimation of the shear velocity of homogeneous biomaterials," *Physics in Medicine and Biology* 49 911-22 (2004), by Wu Z., Taylor L S., Rubens D J., Parker K J., Wu et al. describe inducing a shear wave of known frequency in the medium and determining the shear modulus by estimating the shear wavelength.

An alternative strategy for determining shear modulus, proposed here, is to create a shear wave of known wavelength and measure its frequency. A shear wave with particle motion in the z direction generated by a body force $f_z$ is governed by the inhomogeneous equation:

$$\rho \frac{\partial^2 u_z}{\partial t^2} - G \nabla^2 u_z = f_z. \tag{2}$$

Consider the application of an impulsive body force, as from a quick burst of ultrasound, of the form:

$$f_z = \delta(t) F(x,y,z) \tag{3}$$

in a material initially at rest. The practical utility of the impulse is in approximating a force that occurs on a time scale much shorter than any other of interest in the problem. In the present problem the forcing function pulse can be considered an impulse if its duration is much shorter than the period of the shear wave it ultimately excites. For shear waves of on the order of a few kilohertz, this implies a pulse duration of 100 µs or less can be approximated as an impulse.

Treating the force as an impulsive in time, the applied force will exist only at t=0. Since the applied force will be zero for t>0. the shear wave will be governed by the homogenous equation for time t>0, and its form will be determined by the initial displacement and velocity. The material velocity $\partial u/\partial t$ at time $0^+$, the instant after the application of the impulsive force, may be determined by substituting $f_z$ into Equation (2) and integrating with respect to time, $$\int_{-\infty}^{0^+} \left( \rho \frac{\partial^2 u_z}{\partial t^2} - G \nabla^2 u_z \right) dt = \int_{-\infty}^{0^+} \delta(t) F(x, y, z) dt. \tag{4}$$

At time $t=0^+$, because $u_z=0$ at $t=0^-$ and cannot change instantaneously, the $G\nabla^2 u_z$ term is zero. The velocity at time $0^+$ is then $$\rho \frac{\partial u_z}{\partial t} = F(x, y, z), \quad (5)$$

that is, the initial velocity after the application of the impulsive force is proportional to the forcing function.

The propagation of the wave for $t>0$ may now be calculated using Equation (1) and the initial conditions just determined. For the sake of simplicity let us first consider forces and displacements that vary only with x and t. In this case Equation (1) simplifies to the one-dimensional equation $$\rho \frac{\partial^2 u_z}{\partial t^2} - G \frac{\partial^2 u_z}{\partial x^2} = 0. \quad (6)$$

The solution of this equation for $t>0$ given initial displacement $u_z=0$ and initial velocity $F(x)$ is:

$$u_z(x, t) = \frac{1}{2c} \int_{x-ct}^{x+ct} F(\tau) d\tau$$

Differentiating with respect to t to obtain the material velocity $v_z = \partial u_z / \partial t$ we find that $$v_z(x, t) = \frac{1}{2} \{F(x + ct) + F(x - ct)\}, (t > 0), \quad (7)$$

that is, a wave propagating in the positive and negative x direction whose form is a replica of the forcing function $F(x)$.

Suppose a forcing function as in Equation (3) with $F(x)=1+\cos kx$ is applied. The material velocity at position x will be given by Equation (7) and simplifies to $v_z(x,t)=1+\cos(kx)\cos(\omega t), (t>0),$ where $$\omega = kc = \sqrt{\frac{k^2 G}{\rho}}. \quad (8)$$

This velocity signal may be high-pass filtered to remove the DC component.

Measurement of the frequency of oscillation of the velocity function provides an estimate of the of the shear modulus G, since the other quantities in Equation (8) are known. A somewhat more realistic forcing function would have the form $F(x)=(1+\cos kx)\psi(x)$ where $\psi(x)$ is a smoothly varying envelope function. In this case the velocity signal would be modulated by the envelope function. A suitable choice of envelope function (e.g. Gaussian) will leave the measured frequency unchanged. The result for an arbitrarily shaped forcing function $F(x,y,z)$ is not calculated in this work, but simulated using finite element methods.

SUMMARY OF THE INVENTION

It is therefore an object of the invention to provide a technique that provides a real-time, non-invasive, quantitative measurement of the local shear modulus (stiffness) of tissue.

Another object of the invention is to provide a technique that has all the ARFI advantages but with a quantitative measure of stiffness including when the stiffness is diffuse, i.e., not well defined in any one area.

To achieve the above and other objects, according to the present invention, there is provided a method for determining a shear modulus of a material, wherein an acoustic radiation force is used impulsively to apply a disturbance of known spatial frequency in a medium of unknown shear modulus and known density. The disturbance gives rise to a shear wave, the velocity and temporal frequency of which are directly related to the shear modulus at the initial point of disturbance. Standard ultrasonic motion tracking methods may be used to determine this temporal frequency and thus the local shear modulus. Because the temporal, rather than spatial, frequency of the shear wave is calculated, observations of the tissue displacement can be made at a single point with no need to calculate spatial derivatives of displacement. In addition, calculations of temporal frequency may be made at several points and averaged to improve the determination, since the temporal frequency of the shear wave is fixed by the value of shear modulus at the point of excitation and does not change with propagation of the shear wave.

The present invention, thus, provides a quantitative measurement of the local shear modulus of tissue using a Spatially Modulated Acoustic Radiation Force Impulse (SM-ARFI). The SM-ARFI technique in the present invention is more advantageous over the known ARFI technique because it includes all the advantages of an ARFI provides, plus providing a quantitative measurement of the shear modulus of the tissue.

Two papers related to the present invention have been published, whose disclosures are hereby incorporated by reference in their entireties into the present application:

"Shear modulus estimation by application of spatially modulated impulsive acoustic radiation force" by Stephen McAleavey, Manoj Menon, and Jerrod Orszulak, published in Ultrasonic Imaging 29, 87-104 (2007).

"Direct Estimation of Shear Modulus using Spatially Modulated Acoustic Radiation Force Impulses", by Stephen McAleavey and Manoj Menon, 2007 IEEE Ultrasonics Symposium, Oct. 28, 2007.

BRIEF DESCRIPTION OF THE DRAWINGS

A preferred embodiment of the invention will be set forth in detail with reference to the drawings, in which:

FIGS. 10(a)-(h) show plots of velocity vs. position in a uniform G=1 kPa phantom in response to forcing functions generated by 3 MHz focused linear array, wherein FIGS. 10(a)-(d) are results from using the Focal Fraunhofer method with a 2 mm (FIGS. 10(a) and (b)) or 4 mm (FIGS. 10(c)-(d)) standard deviation of the lateral pressure profile. FIGS. 10(e)-(h) are results from using the intersection Gaussian beams with 2 mm (FIGS. 10(e) and (f)) or 4 mm (FIGS. 10(g) and (h)) standard deviation of the Gaussian describing the beam aperture.

DETAILED DESCRIPTION OF THE PREFERRED EMBODIMENT

A preferred embodiment of the invention will be set forth in detail with reference to the drawings, in which like reference numerals refer to like elements or steps throughout.

Many non-limiting aspects of the present invention can be better understood with reference to the following figures. The components in the figures are not necessarily to scale, emphasis instead being placed upon clearly illustrating the principles of the present invention. Further, in describing the non-limiting aspects of the present invention illustrated in the figures, specific terminology is resorted to for the sake of clarity. Each specific term, however, is meant to include all technical equivalents that operate in a similar manner to accomplish a similar purpose. The present invention, therefore, is not limited to the specific terms so selected.

Figure 1:
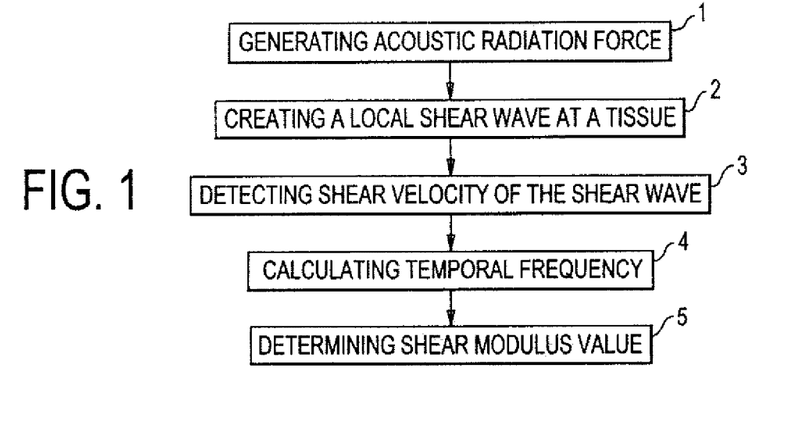
FIG. 1 shows a flow chart of an exemplary method for determining the shear modulus of a material in accordance with a non-limiting embodiment of the present invention.

FIG. 1 shows an exemplary flow chart of a preferred embodiment of the method for determining the shear modulus of a material such as human or animal soft tissue. In step 1, an acoustic radiation force impulse is used to generate disturbance or displacements in a tissue which has a known density ρ and unknown shear modulus value G. In step 2, the disturbance at a point in the tissue creates a localized shear wave of desired, known wavelength λ and spatial frequency (wave number) k, where k and λ are related by k=2π/λ. In step 3, the propagation, i.e., shear velocity $c_s$, of the local shear wave is detected by ultrasonic or MRI devices. In step 4, the temporal frequency of the shear wave is calculated using the equation:

$$f_s = c_s/\lambda_s$$

It is well known that the shear modulus G of a linear elastic material such as a soft tissue with density ρ is related to the speed of shear wave propagation $c_s$ by:

$$c = \sqrt{G/\rho}$$

In terms of the local shear modulus, the temporal frequency of the shear wave is:

$$f_s = \sqrt{\frac{G}{\lambda_s^2 \rho}}.$$

From the equation above, the local shear modulus G can be calculated using the following equation:

$$G = \rho f_s^2 \lambda_s^2$$

In step 5, the local shear modulus G is determined using the known wavelength λ, known tissue density ρ and determined temporal frequency $f_s$.

Determining the temporal frequency $f_s$ is much easier than determining the local wavelength of a shear wave. Furthermore, it is well known that the temporal frequency of a shear wave remains unchanged even as the shear wave propagates into regions with other values of shear modulus G due to the necessity of material continuity during wave propagation with the spatial frequency k varying to satisfy the wave equation. Thus, the temporal frequency $f_s$ of the shear wave carries information about the shear modulus of the point of excitation. This frequency is unchanged even if the observation point is located in a region of differing shear modulus.

Regarding the temporal frequency $f_s$, standard ultrasonic motion tracking methods may be used to determine the temporal frequency and thus the local shear modulus. Because the temporal, rather than spatial, frequency of the shear wave is calculated, observations of the tissue displacement can be made at a single point with no need to calculate spatial derivatives of displacement.

In FIG. 1, the calculation of temporal frequency in step 4 is made at a single point in the tissue. However, the calculation of the temporal frequency may be made at several points and averaged to improve the determination because the temporal frequency of the shear wave is fixed by the value of shear modulus at the point of excitation and does not change with propagation of the shear wave.

Figure 2:
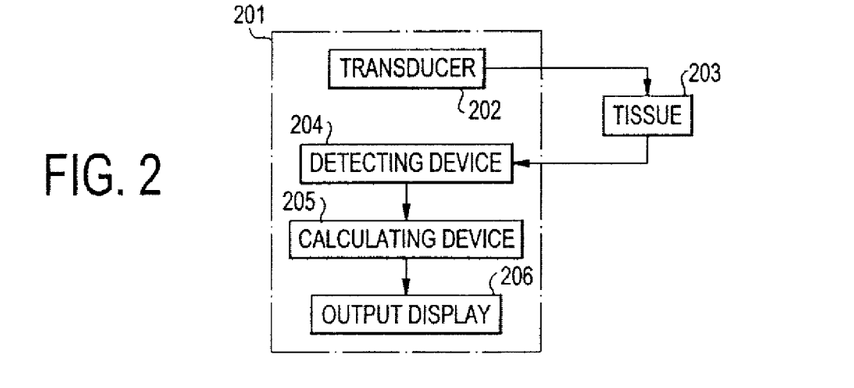
FIG. 2 shows a block diagram of an exemplary device that carries out the exemplary method shown in FIG. 1.

FIG. 2 shows an exemplary block diagram of a device 201 that carries out the method for determining the shear modulus of a soft tissue in accordance to the preferred embodiment. The device 201 may include an element 202 such as a transducer to generate acoustic radiation force impulses to the soft tissue 203. In response to the disturbance caused by the acoustic radiation force, a shear wave is generated from the soft tissue 203. The device 201 further includes a detector 204 that detects the temporal frequency of the shear wave from the soft tissue. The calculating device 205 calculates the shear modulus using the detected temporal frequency, known wave length, and known density of the soft tissue as disclosed above. The device further includes an output 206 connected to the calculating device to display the value of the shear modulus of the tissue and other desired values.

A scanner from manufacturer Siemens such as a Siemens Antares may be used as the device 201. The scanner is programmed by the users to provide custom beam sequences, using a VF7-3 linear array transducer, and to collect the RF echo data. The device 201 can also be an ultrasound equipment from companies such as GE and Philips.

Figure 3:
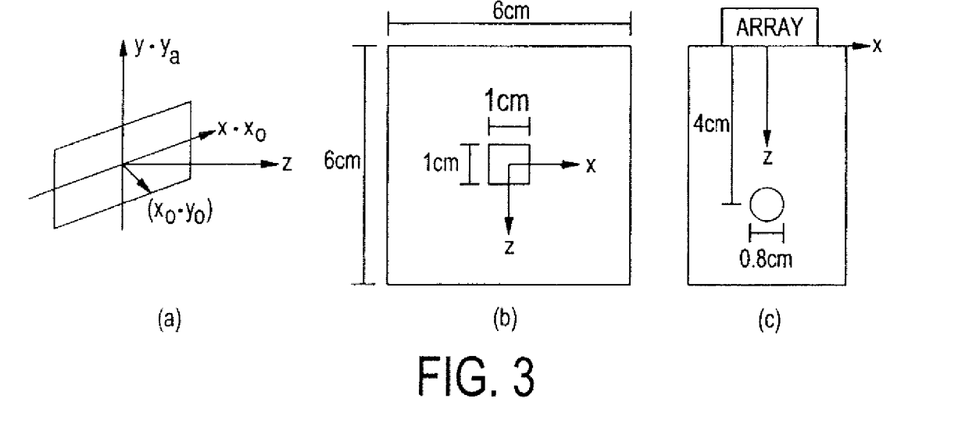
FIG. 3(a) illustrates a geometry for Fraunhoffer transducer model.
FIG. 3(b) shows an illustrative model for Gaussian forcing function simulation.
FIG. 3(c) shows an illustrative model for linear array forcing functions.

Regarding step 1 in FIG. 1 above, the use of acoustic radiation force to generate displacements in tissue or a medium is known in the art. Acoustic radiation force acts as a body force in an attenuating medium. For plane wave excitation the force is given by F=2aI/$c_l$, where a is the material attenuation coefficient, I the acoustic intensity, and $c_l$ the longitudinal speed of sound. This expression has also been found to give qualitatively good agreement with experimental measurements when the intensity is a function of position, as in the beam generated by a focused ultrasound transducer. Therefore by varying the intensity as a function of position the radiation force may likewise be varied. Linear phased arrays provide great control over the formation of ultrasound beams and the acoustic intensity as a function of position. Push beam intensity patterns of a specific lateral spatial frequency may be created though modulation of the relative phase and/or amplitude of array elements. Several methods are described in the literature for creating such a pattern. We describe four of these methods here:

The first is the Focal Fraunhofer approach. It is well known that in the far field of an unfocused transducer or in the focal zone of a focused transducer the lateral pressure variation is the Fourier transform of the apodization function of the aperture, $$p(x,y,z) = P_0 \lambda_l^2 z^2 \iint_S A(\lambda z x_0, \lambda z y_0) e^{-j2\pi x x_0} e^{-j2\pi y y_0} dx_0 dy_0$$

where $A(x, y)$ is the complex apodization including the phase shift for focusing and $$P_0 = \frac{j\rho c_l v_0 e^{j2\pi f_l t - k_l z} e^{-jk_l(x^2+y^2)/2z}}{\lambda_l z}$$

where $v_0$ is the peak velocity amplitude of the transducer, and $k_l$, $c_l$, and $l_l$ are the wavenumber, sound speed, and wavelength of the longitudinal (i.e. ultrasound) wave. The aperture geometry is illustrated in FIG. 3a. For separable $A(x, y) = A_x(x)A_y(y)$ the pressure in the $y=0$ plane is simply $$p(x,z) = P_0 P_y \lambda_l z \int A_x(\lambda_l z x_0) e^{-j2\pi x x_0} dx_0 \quad (9)$$

where $P_y = \int A_y(y_0) dy_0$. Therefore a sinusoidal oscillation of pressure may be induced by an apodization consisting of a pair of impulses. This method was employed by Anderson to generate a laterally varying pressure for estimation of the lateral component of blood flow velocity. In order to radiate any significant energy, an apodization consisting of a pair of well-localized windows is used. For instance, an apodization consisting of a sum of Gaussians displaced from the beam axis of the form $$A(x_0) = e^{-(x_0-d)^2/2s^2} + e^{-(x_0+d)^2/2s^2} \quad (10)$$

gives a pressure at the focus $z_f$ of the form $$p(x) = P_0 P_y 2s\sqrt{2\pi} e^{-(ksx)^2/2z_f^2} \cos(kxd/z_f) \quad (11)$$

and an intensity of $$I(x) = I_0 4\pi s^2 e^{-(ksx/z_f)^2}(1 + \cos(2kxd/z_f)) \quad (12)$$

The limitation of this technique can be seen in Equation (12). As s is increased, allowing more energy to be put into the beam, the focal region narrows proportionately. This relationship makes it difficult to create a high pressure in the focal zone while also generating a lateral pressure distribution of well-defined spatial frequency. For the intensity signal $$I(x) = I_0 4\pi \frac{z^2}{2k^2\sigma^2} e^{-x^2/2\sigma^2}(1 + \cos(2\pi x/\lambda_s))$$

the apodization parameters are $$d = \frac{z_f \lambda_0}{2\lambda_s} \text{ and } s = \frac{\sqrt{2}\lambda z_f}{4\pi\sigma}.$$

A second method, the intersecting plane wave approach, is to use intersecting unfocused beams of identical frequency traveling at an oblique angle to each other. The simplest expression of this idea is a pair of plane waves propagating at angles of $\pm\theta$ to the z axis, $$p(x,t) = p_0 \cos(2\pi f_l t + k_l(z\cos\theta - x\sin\theta)) + p_0 \cos(2\pi f_l t + k_l(z\cos\theta + x\sin\theta))$$

which is equal to $$p(x,t) = 2p_0 \cos(2\pi f_l t + z\cos\theta)\cos(k_l x \sin\theta).$$

Such plane waves set up a lateral pressure variation of wavelength $l_s = l_l/\sin q$. The intensity is given by $$I(x) = 4P_0^2(1 + \cos(2k_l x \sin\theta))/2 \quad (13)$$

A finite aperture cannot be used to generate plane waves, but a good approximation can be achieved over a limited area by intersecting two unfocused Gaussian beams. Such beams maintain their lateral profile until the near/far transition, when they begin to spread. The advantage of this method compared to the Focal Fraunhofer method is that, while there is no focal gain, a greater number of elements may be used to form the beams while still creating a wide region of excitation.

A third method, the sequential excitation, is to generate the desired intensity distribution sequentially, rather than simultaneously, by firing a number of beams with intensity and foci located so that the sum intensity over the entire sequence is the desired intensity. This method is feasible because the great difference between longitudinal ultrasound wave speed (1540 m/s) and shear wave speed (1-10 m/s) and high ultrasound pulse repetition frequencies that may be used allow an entire beam sequence to be transmitted before the shear wave has propagated appreciably. Indeed, since one need not wait for echoes from the push beam, the PRF may be as high as the reciprocal of the push time at any one location regardless of the desired depth. The advantage of this method is that much greater intensities can be achieved, because a large number of transducer elements may be used to generate each beam in the sequence, unlike the Focal Fraunhofer method, while at the same time beam focusing is implemented to achieve high local intensities, unlike the intersecting plane waves method.

In a fourth method, we apply the constrained least-squares method of Walker and Guenther to determine apodization and phase vectors in terms of $\lambda_1$, $\lambda_s$, and $\sigma_0$. Simultaneously focusing several parallel beams using interlaced apertures, we also consider the generation of multiple lateral foci rather than a pair of intersecting beams. The focusing methods considered will include simple geometric focusing, Gaussian beam phasing/apodization, and interlaced non-diffracting (X-wave) apertures. The results will be evaluated both in terms of maximizing the peak intensity generated by each method in the region of interest and minimizing the intensity outside it.

Of the four methods, the Focal Fraunhofer and Gaussian beam methods are demonstrated in this paper. The result of any of these methods is a lateral modulation of beam intensity of the form $I(x) = (1+\cos k_s x)\psi(x)$ where $\psi(x)$ is a smoothly varying non-negative envelope function. It is important to remember that the spatial frequency of the lateral variation in intensity, $k_s$, is twice the spatial frequency of the pressure variation, due to the squaring of pressure to calculate intensity. The shear wave generated will be of spatial frequency $k_s$.

Simulation will now be described. Two-dimensional finite element models were employed to model the response of tissue to spatially varying acoustic radiation force and the propagation of shear waves from the excitation location. Comsol Multiphysics (Comsol, Inc.) was used to create and analyze the 2D plane-strain model. A mesh pitch of 0.25 mm was used for all models to provide adequate spatial sampling.

The adequacy of this pitch was verified by mesh refinement tests. Tissue was modeled as a linear elastic solid with a density of 1000 kg/m³. Radiation force was modeled as a body force in the direction of beam propagation. Two models were created.

The first model, Gaussian Force Model, depicted in FIG. 3b, was a uniform elastic solid of dimensions 6 cm×6 cm (the equivalent 3D solid having identical properties and forces that do not vary perpendicular to the cross-section shown). The solid was modeled as having a density of 1000 kg/m³, a Poisson's ratio of 0.49, and shear modulus G of 1 kPa. This model was evaluated for Young's modulus values of 3 kPa and 6 kPa (G=1 and 2 kPa). A Raleigh damping model with a=1 and b=0 was used. Lagrange quadratic elements were used. A fixed boundary condition was applied to prevent bulk motion of the model. In this model the radiation force was modeled as a Gaussian-weighted cosine applied for 50 μs and described by $$F_z(x,z)=F_0(1+\cos 2000\pi x)e^{-(x^2+y^2)/(2 \cdot 0.001^2)} \quad (14)$$

where $F_0$ is the peak force. This forcing pattern had a spatial frequency in the x direction of 1 cycle/mm, corresponding to a shear wave frequency $f_s$ of 1 kHz in 1 kPa shear modulus material.

The second model, the Linear Array Model, used forcing functions generated by linear arrays using techniques described in the Description of Related Art section above. In this model the transducer was centered at the origin with the z axis normal to the transducer face. The model was either uniform with a shear modulus of 1 kPa, or included a 0.8 cm diameter 2 kPa lesion centered at a depth of 4 cm. The Poisson's Ratio for this model was 0.4995, and the Raleigh damping coefficients were $\alpha=1$ and $\beta=10^{-5}$. This slightly larger value of b improves the numerical convergence and runtime of the finite element program and does not significantly alter the simulation results. A more realistic model of the applied radiation force was used for this model. The Field II ultrasound simulation program was used to calculate beam patterns for two linear arrays. The arrays had center frequencies of 3 MHz and 5.33 MHz and were simulated using the parameters given in Table 1 below. The simulation geometry is depicted in FIG. 3c.

TABLE 1

Transducer Parameters for Field II Simulations

| | Transducer A | Transducer B |
|---|---|---|
| Frequency | 3.0 MHz | 5.33 MHz |
| Element Pitch | 0.4 mm | 0.2 mm |
| Element Height | 15 mm | 7.5 mm |
| Elevation Focus | 4 cm | 3.75 cm |

Both the Focal Fraunhofer and intersecting Gaussian beam methods were examined. In all cases a lateral intensity modulation of 1 cycle/mm was generated. In the Focal Fraunhofer method simulation the element phasing was selected to form a focus at z=4 cm with transducer A and at z=2 cm with transducer B. The apodization was determined using Equation (12) to generate a cosine-modulated Gaussian intensity profile at the focus. For array A apodizations were calculated for obtaining standard deviations of the Gaussian lateral profile of $s_x=2$ mm and $s_x=4$ mm, while for array B a focal width of $s_x=1$ mm was selected. The intersecting beam method was implemented by generating pairs of Gaussian apertures with standard deviations of s=2 mm and s=4 mm in the case of transducer A and s=1 mm for transducer B. The phase across each aperture was varied linearly to steer the beams by ±q and generate the desired lateral pressure modulation spatial frequency, as given by Equation (13). The distance between the aperture pair centers was selected so the beam axes intersected at z=4 cm for transducer A and z=2 cm for transducer B.

The use of Field II allows comparisons between the intensities achieved by the different beamforming methods. This is especially useful for determining which method will generate the largest intensities (and hence displacements) given a limited maximum drive voltage for each transducer element. A tissue attenuation value of 0.7 dB/cm/MHz was used and non-linear propagation effects were not considered. Intensity values for a 50 μs pushing pulse were calculated on a 10 points/mm grid in the scan (y=0) plane. The intensities at each point were converted to a body force using the F(x, y)=2aI(x, y)/c relationship with the direction of the force away from the transducer.

Figure 4:
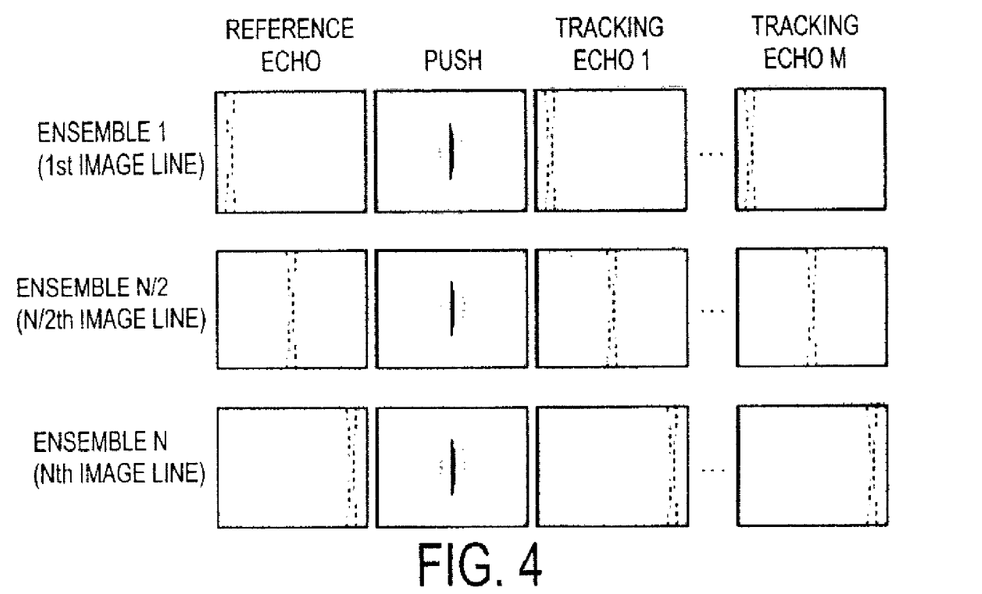
FIG. 4 shows SMURF pulse sequence.

In vitro experiments were performed with a Siemens Antares ultrasound scanner (Siemens Medical Solutions USA, Ultrasound Group). A VF7-3 linear array transducer, which roughly matches the characteristics of Transducer B in Table 1 in FIG. 12 was used. A custom beam sequence, illustrated in FIG. 4, was created to generate a modulated radiation force and track the resulting shear waves. The beam sequence is similar to the shear wave tracking sequence described by Nightingale K., McAleavey S., and Trahey G. in "Shear-wave generation using acoustic radiation force: In vivo and ex vivo results," *Ultrasound in Medicine and Biology* 29, 1715-23, (2003). The pushing beam is fired at the same location for all ensembles, while the tracking sequence is swept across the region of interest. By repeatedly firing the pushing pulse at a single location and tracking at multiple locations a composite sequence is developed which tracks the progress of the shear wave through the entire region of interest. This sequence allowed the propagation of the induced shear wave to be visualized. However, such visualization is not necessary for determining frequency of the induced shear wave. The shear wave frequency and shear modulus may be determined from a single excitation and tracking of a single point.

Tracking and pushing beams were both focused at a depth of 2 cm. The tracking beams employed a raised-cosine apodization. The pushing beam was generated using a pair of rectangularly-apodized apertures with linear phasing across each to steer the beams to intersection and generate a 1 cycle/mm lateral intensity variation. The pushing pulse was 200 cycles long with a center frequency of 6.67 MHz. A total of 64 elements were used, 32 each for the left and right apertures.

Tissue mimicking phantoms, similar to those described by Hall T. J., Bilgen M., Insana M. F., and Krouskop T. A. in "Phantom materials for elastography," *IEEE Transactions on Ultrasonics, Ferroelectronics and Frequency Control*, 44, 1355-65, (1997), were used for in vitro testing of the method. Two phantoms were constructed, one "soft" and one "stiff". The soft phantom had a gelatin concentration of 33 g/liter water, while the stiff phantom had a concentration of 99 g/liter water. Graphite powder at a concentration of 160 grams/liter was added to act as a scattering agent, n-propanol was added at a concentration of 50 ml/liter to adjust the longitudinal sound speed of the phantom, and gluteraldehyde at 10 mL/liter to cross-link the gelatin. The phantoms were nearly cylindrical, with a top diameter of 6.5 cm, bottom diameter of 8 cm, and height of 7 cm.

The shear modulus of each phantom was determined using unconfined cyclic loading to estimate Young's modulus. The shear modulus can be found from the Young's Modulus E using the relationship G=E/2(1+n), where n is Poisson's ratio, assumed here to be 0.5 (incompressible). The entire phantom was placed in between two oil-coated platens of a MTS Sintech Material Testing Workstation (MTS System Corporation). The phantoms underwent compression up to a 5% strain at a rate of 2 mm/s while the force was measured using a 5N load cell. Young's modulus was determined from the slope of the stress-strain curve in the 3-5% strain region to avoid measurement error due to contact non-uniformity between the phantom and platens.

For the results of the Gaussian Model simulation, the velocity versus time for the Gaussian forcing function of Equation (14) in a uniform G=1 kPa function at the points (x,z)=(0,0, (3,0), and (7,0) mm is shown in FIG. 5a-c. In all cases the time between wave peaks is 1 ms, as expected from Equation (8). Slight disturbances due to the reflection of a longitudinal wave are visible in the plots. These are discernible due to the relatively low Poisson's ratio (0.49) used in the model. Values of Poisson's ratio closer to 0.5 would diminish the amplitude of the longitudinal wave.

Graphs of velocity versus time for the same Gaussian forcing function acting at the center of a G=2 kPa region 1 cm$^2$ enclosed in a G=1 kPa background (see FIGS. 3a-c) are presented in FIG. 5d-f at the same spatial locations as plots a-c. We note that the doubling of shear modulus has resulted in a $\sqrt{2}$ increase in the temporal frequency of the wave, estimated from the peak-peak interval, as expected from Equation (8). The peak of the wave arrives at the 3 mm point at 2.1 ms in keeping with the 1.4 m/s velocity within the lesion. Notice also that the temporal frequency of the wave does not change as it propagates from the G=2 kPa region to the G=1 kPa region, as expected. The peak arrives at the 7 mm point at 5.6 ms, as expected for propagation through 5 mm at 1.4 m/s and 2 mm at 1 m/s.

Figure 5:
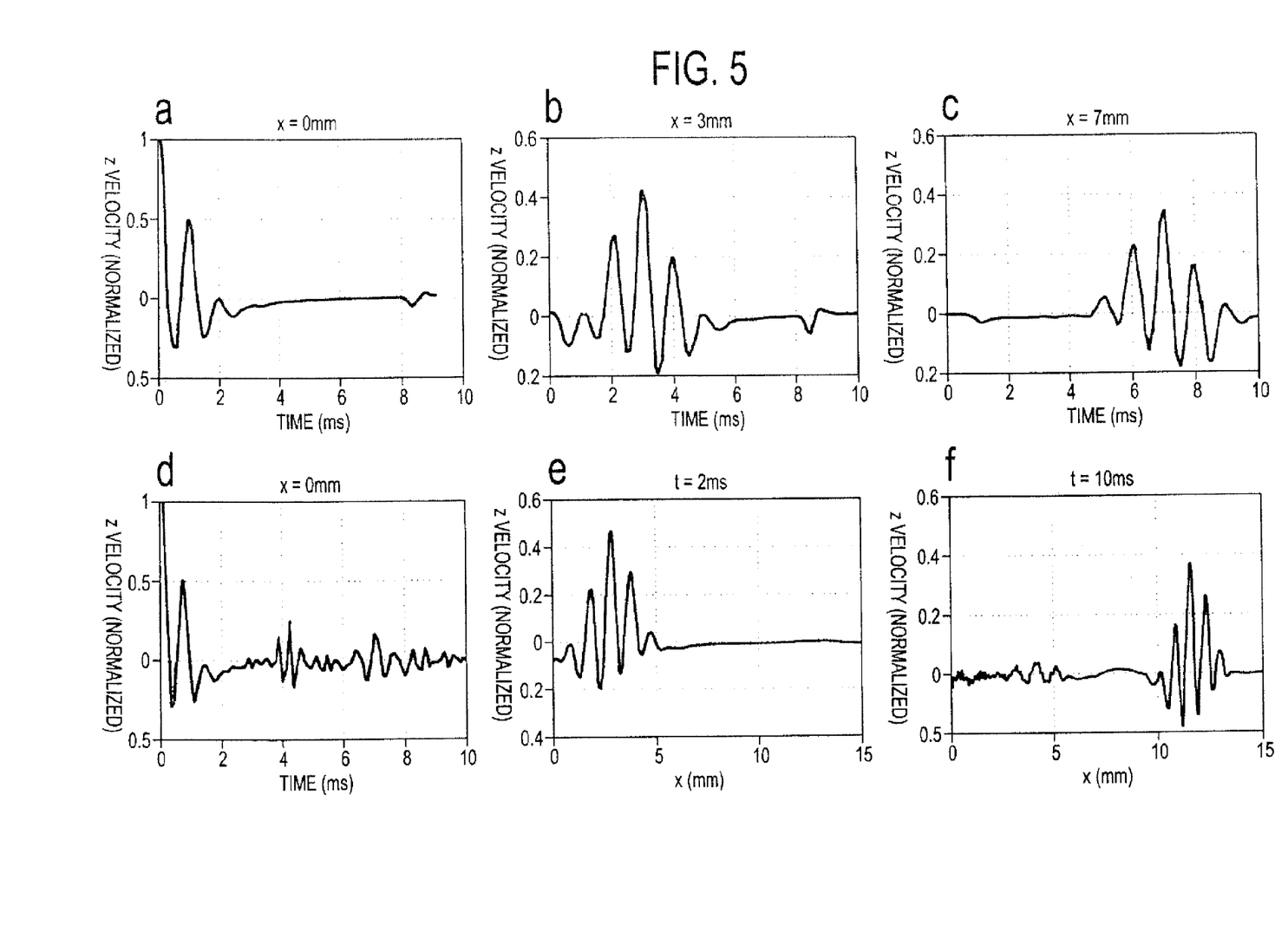
FIGS. 5(a)-(c) show graphs of particle velocity vs. time for a uniform medium with shear modulus G=1 kPa and density r=1000 kg/m$^3$.
FIGS. 5(d)-(f) show graphs of particle velocity vs. time in a phantom with a G=2 kPa inclusion.

FIG. 5 reveals that the velocity wave generated by the Gaussian forcing function contains negative velocity values. The one dimensional model of Equation (7) suggests that, since the forcing function is non-negative, the velocity wave should likewise be zero or greater. The discrepancy is due to the fact that the forcing function used varies both in x and z, and the Laplacian in Equation (1) will contain a non-zero $\partial^2 u_z/\partial z^2$ term. In the one-dimensional case the forcing function and displacement do not vary with z and the $\partial^2 u_z/\partial z^2$ is zero. In both cases the essential aspect of the forcing function, the imposed wavelength, is maintained.

Figure 6:
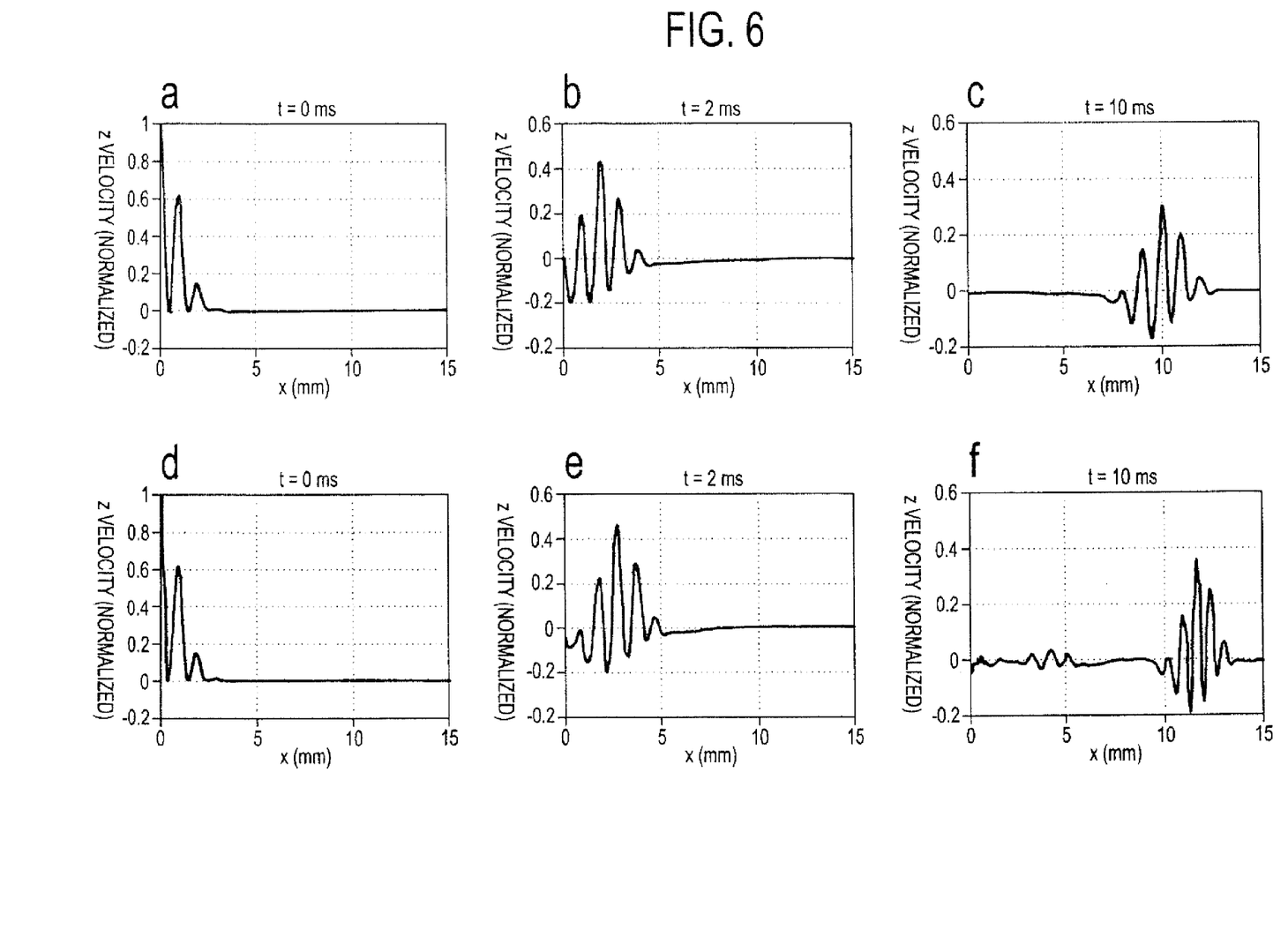
FIG. 6(a)-(c) show graphs of particle velocity vs. lateral position (x) in the direction of the forcing function in a uniform G=1 kPa medium at 0 ms, 2 ms, and 10 ms, respectively, after application of the pushing pulse.
FIGS. 6(d)-(f) show graphs of particle velocity vs. position at 0 ms, 2 ms and 10 ms, respectively, in a phantom with a G=2 kPa inclusion.

Velocity as a function of x in the uniform model is plotted in FIGS. 6a-c at t=0, 2 and 10 ms. The wave propagating through a uniform G=1 kPa material maintains its 1 mm wavelength. In FIGS. 6d-f the contraction of wavelength by a factor of $1/\sqrt{2}$ as the wave propagates from the G=2 kPa (x<5 mm) to the G=1 kPa (x>5 mm) is visible. Also visible in FIG. 6f at about 4 mm is the a reflected wave from the left-hand boundary of the lesion. That initial velocity matches the forcing function can be seen clearly in FIGS. 4a and d. The initial velocity is also insensitive to the modulus of the lesion. This follows from Equation (4), where the shear modulus multiplies only the Laplacian of displacement, which is zero at time zero.

For the results of the linear array model simulation, the intensity patterns generated by the 3 MHz and 5.33 MHz linear arrays as calculated by Field II are plotted on a linear grayscale in FIGS. 7a-d and FIG. 8. For clarity each plot is normalized to the maximum calculated intensity in the field of view. The fields generated by the focal Fraunhofer method (FIGS. 7a and b, FIG. 8 left) show a pronounced broadening with increasing distance from the transducer. This leads to a depth-dependent excitation wavelength, which would cause a bias in the shear modulus estimates were it not accounted for. The intersecting Gaussian beam method shows much smaller broadening, since the region of interest (around z=4 cm for the 3 MHz array and z=2 cm for the 5.33 MHz array) is in or close to the near field of the individual Gaussian apertures.

Another significant difference between the two forcing function generation methods is in the relative near-field intensities. Compared to the intersecting Gaussian beams methods, the near-field intensities generated by the Focal Fraunhofer method are greater in proportion to the peak intensity generated at the focus. This result shows up the limitation of the Focal Fraunhofer method, namely that a small number of elements may be used to generate the desired lateral intensity modulation, and that as a consequence a greater proportion of the push-beam energy will be lost to the near field.

Figure 7:
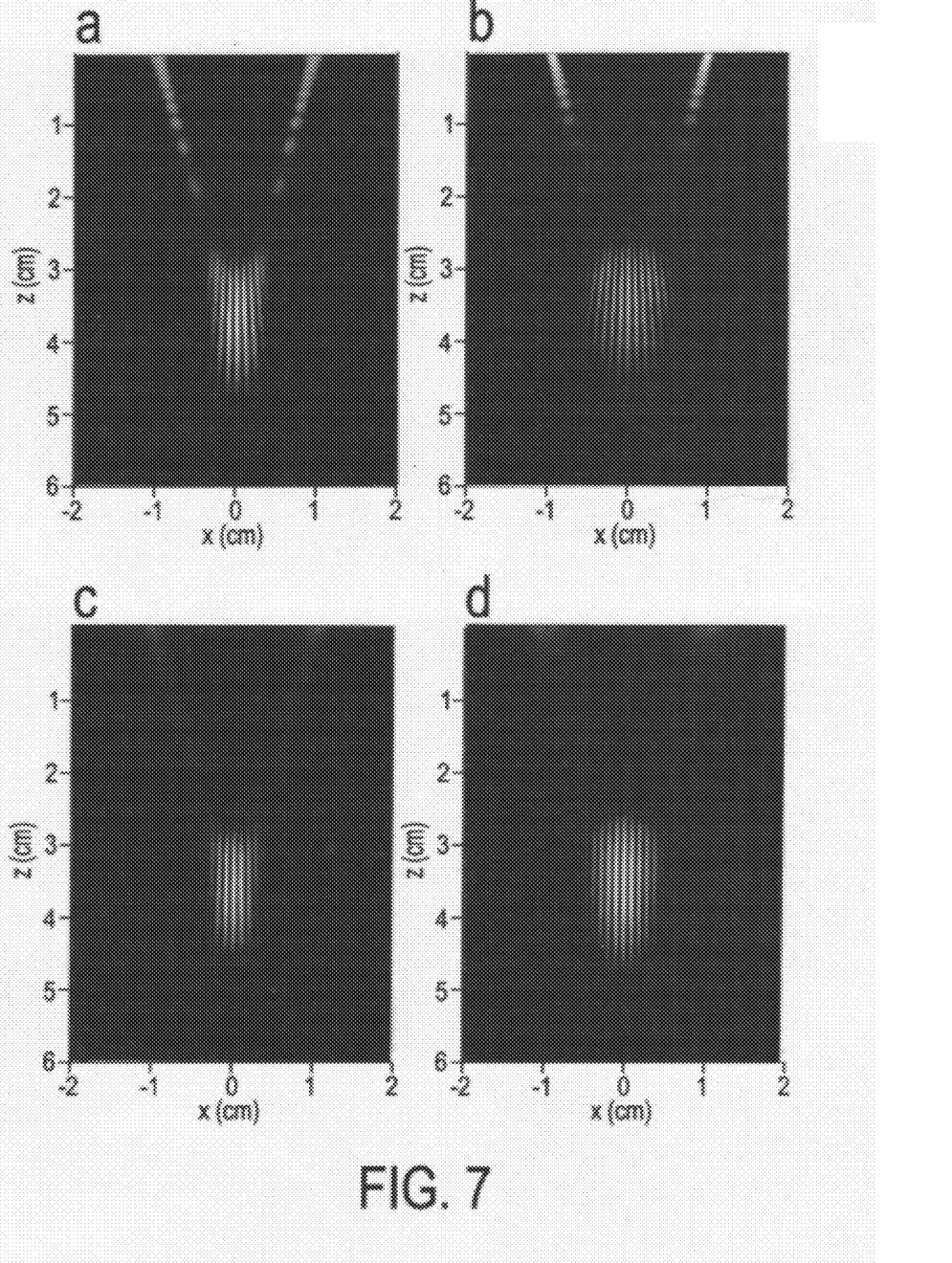
FIGS. 7(a)-(d) show plots of acoustic field intensity generated by 3 MHz linear array.
Figure 8:
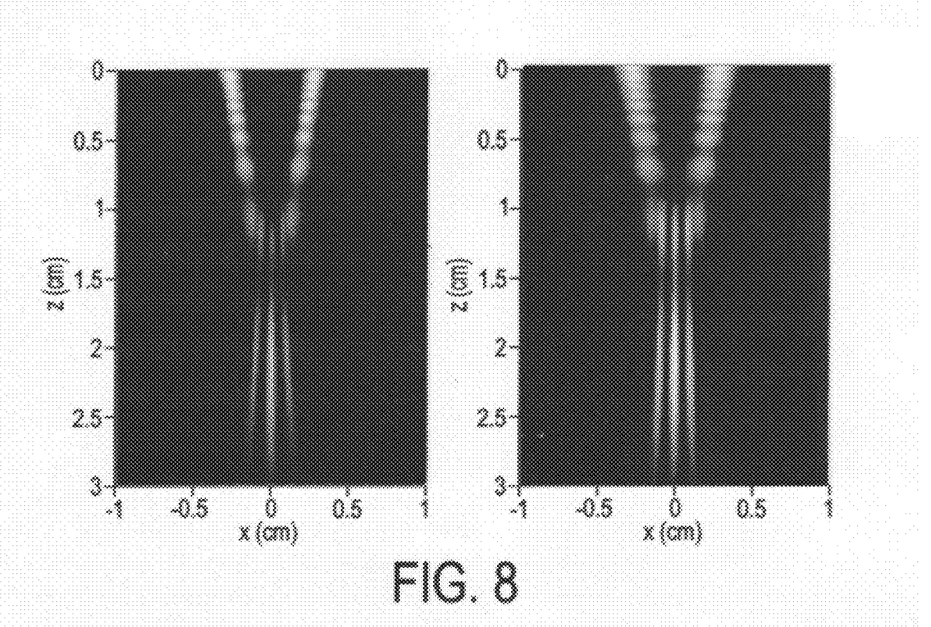
FIG. 8 shows plots of acoustic field intensity generated by 5.33 MHz linear array.
Figure 9:
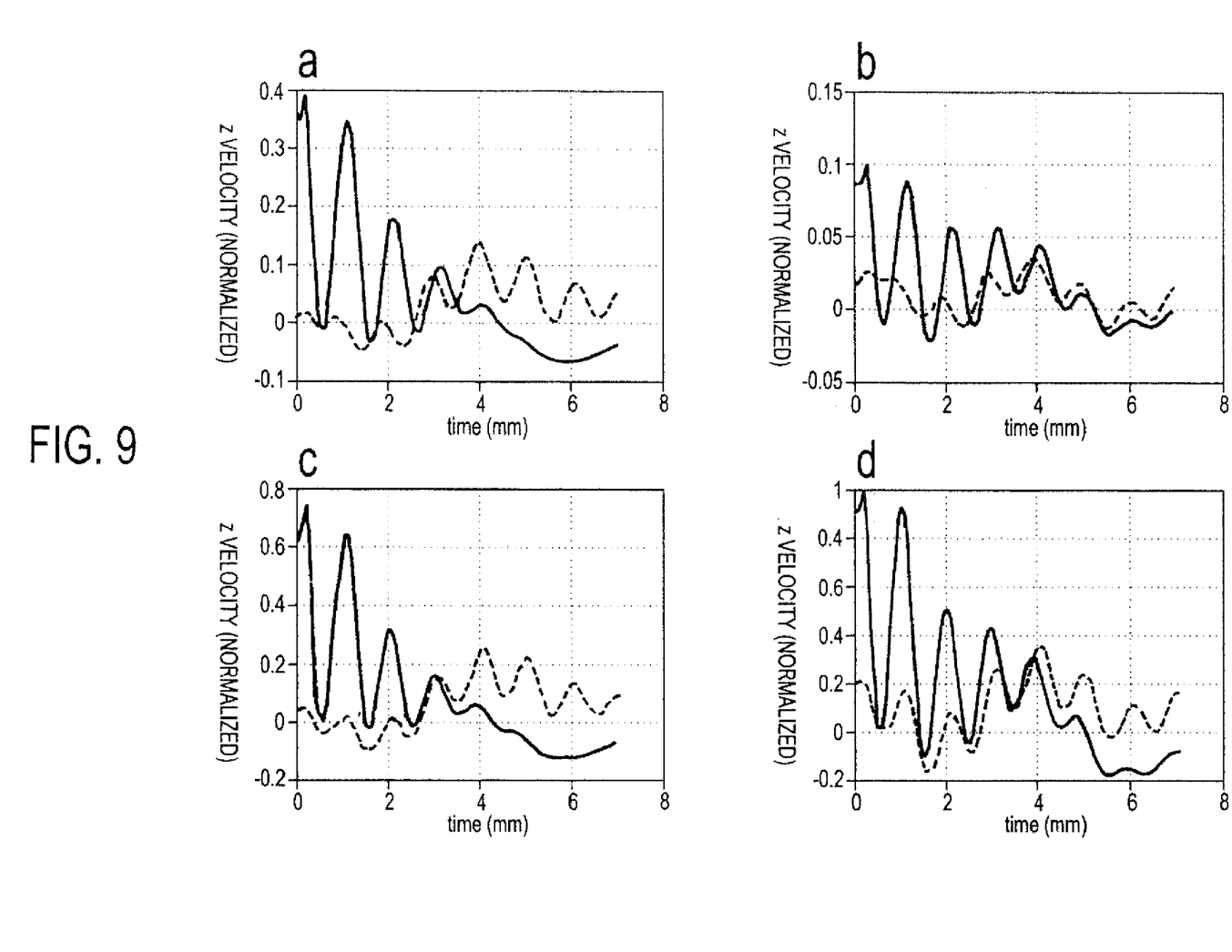
FIGS. 9(a)-(b) show plots of velocity through time in a uniform G=1 kPa phantom in response to forcing functions generated by 3 MHz focused linear array, using the Focal Fraunhofer method at (a) $s_{focus}$=2 mm and (b) $s_{focus}$=4 mm.
FIGS. 9(c)-(d) show plots of velocity through time in a uniform G=1 kPa phantom in response to forcing functions generated by 3 MHz focused linear array, using the Intersecting Gaussian beams at (c) $s_{beam}$=2 mm and (d) $s_{beam}$=4 mm.
Figure 10:
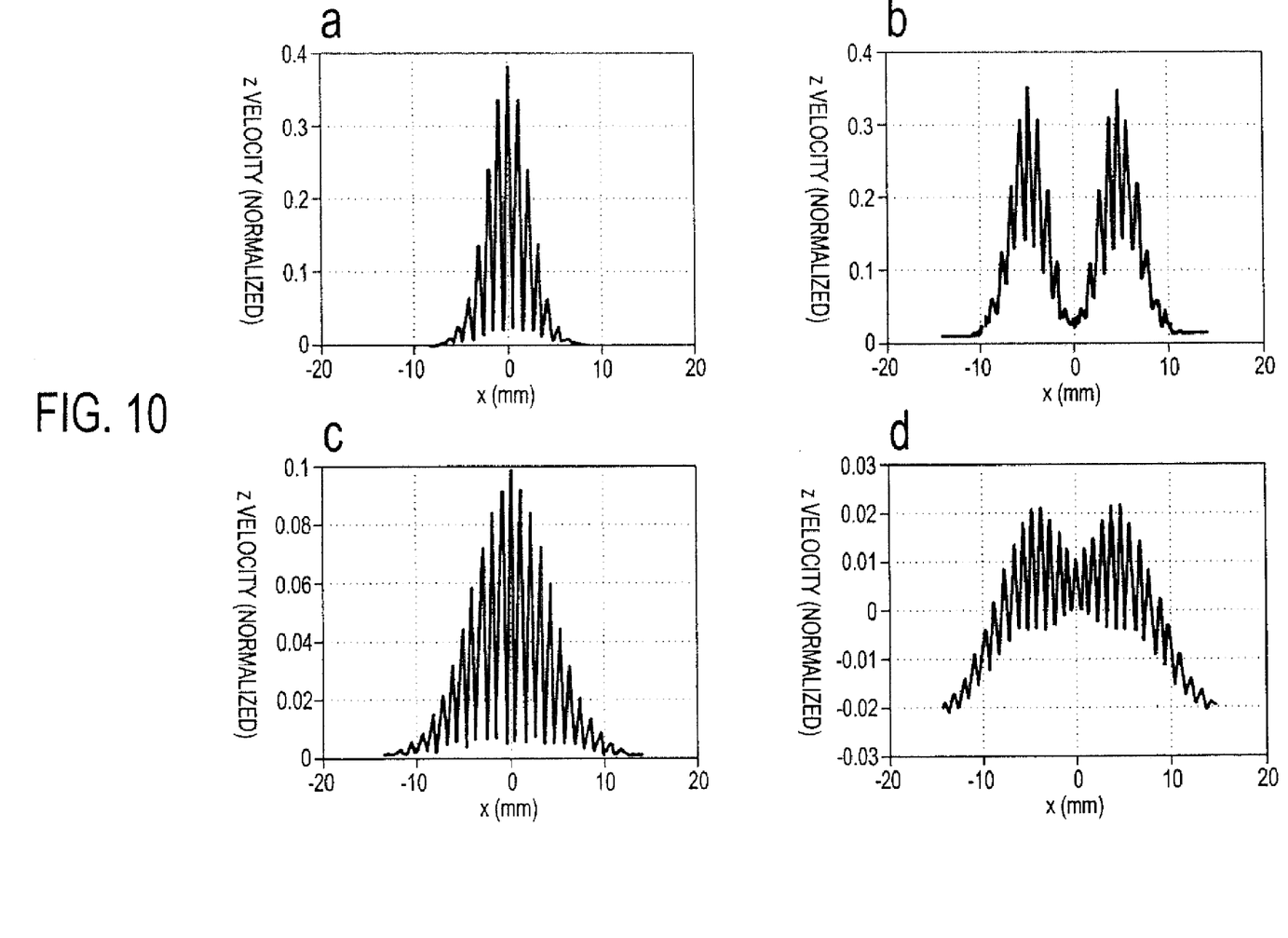

The response of the uniform G=1 kPa phantom to the forcing functions of FIG. 7 is shown in FIGS. 9a-d as a function of time and in FIG. 10 as a function of lateral position. In all cases the greater force exerted by the intersecting Gaussian beams method is evident, increasingly so as the width of the region of excitation is increased. The initial velocities are observed to be a good match to the lateral distribution of the beam intensities. The response through time at two points ((0,4) cm and (0.5,4) cm) near the "focus" of the pushing beams is shown in FIGS. 9a-d. In all cases the expected 1 kHz frequency is observed. The 1 kHz signal rides on top of a low-frequency component due to the axial and lateral variation in the envelope of the forcing function, which may be removed by high-pass filtering. The evolution of the shape of the velocity wave as it propagates from its initial non-zero form is illustrated in FIG. 10, where velocity as a function of position is plotted at 0 and 5 ms after the application of the forcing function.

Figure 11:
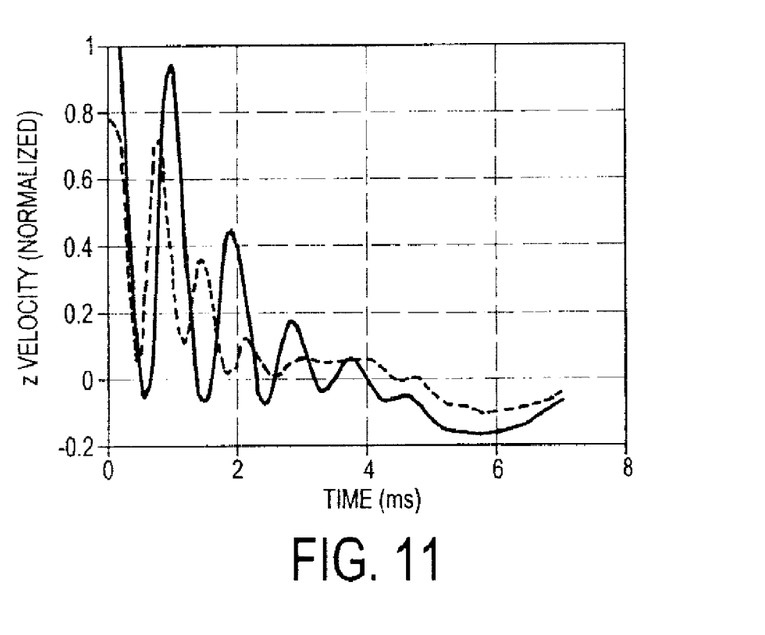
FIG. 11 shows a plot of velocity vs. time in response to 3 MHz focused linear array in the lesion model with $G_{lesion}$=2 kPa and $G_{background}$=1 kPa.

The velocity through time in the 0.8 cm lesion model is shown in FIG. 11. The frequency of the velocity wave at the center of the lesion and at a point 2 mm outside are seen to vary by the expected factor of $\sqrt{2}$. This reassuringly illustrates that, though the forced region is significantly larger than the lesion, it is possible to distinguish the lesion from the background by measuring the local vibration frequency. Results obtained with the other pushing beams were similar.

For the in vitro results, the two gelatin phantoms had Young's modulus values of 16.9±0.5 kPa and 4.6±0.2 kPa, as estimated by the MTS measurement system. These correspond to shear moduli of 5.6 kPa and 1.5 kPa, determined by the relationship G=E/2(1+n), where we have assumed the phantom is incompressible and Poisson's ratio n=0.5. The experimentally measured velocity though time in response to the 1 cycle/mm pushing beam in the two gelatin phantoms. The value of shear modulus for each phantom is determined using Equation (8), with k=2p/l=200 pm$^{-1}$ and density r=1000 kg/m$^3$. The period of oscillation of the soft phantom is estimated to be 0.83 ms (based on peak-to-peak time), corresponding to a frequency of 1.2 kHz and a shear modulus of 1.4 kPa. The stiff phantom has an estimated modulus of 5.8 kPa. Both values show good agreement with the MTS measurements.

The success of the method in the present invention depends on the ability to generate a nearly impulsive forcing function with a well-defined spatial frequency. The approximation of the forcing function is well justified for pulses on the order of 10-100 µs, since the induced wave will only propagate a small fraction of a wavelength during the excitation period. For instance, a l=1 mm wave in a G=2 kPa medium will propagate only 71 µm or 1/14 of a wavelength over the duration of a 50 µs pushing pulse. Two methods have been demonstrated here based on either intersecting Gaussian beams or the Fraunhofer approximation. While either method can generate the desired spatial frequency, for a given peak pressure from any given transducer element, the Gaussian beam method is able to deliver a higher intensity to the region of interest for the model considered here, due to the greater utilization of elements in the aperture. In "Supersonic shear imaging: A new technique for soft tissue elasticity mapping" *IEEE Transactions on Ultrasonics, Ferroelectronics and Frequency Control* 51, 396-409, (2004), Bercoff J., Tanter M., and Fink M. have demonstrated the synthesis of spatially extended shear wave sources using radiation force from a sequence of pushing beams. It may be feasible to create spatially modulated beams of well defined spatial frequency using this method as well. The pulse-repetition frequency used for sequentially "painting" the spatially modulated pushing beam may be very high, since there is no requirement to wait for echoes to return from any depth. Therefore, the effective pulse repetition period could be on the order of the duration of an individual pushing beam, 50 µs, creating a nearly impulsive force from a sequence of pushes.

The analysis presented here assumes that propagation of shear waves through the medium to be interrogated is purely elastic and lossless. Tissue is known to be viscoelastic. Among the consequences of viscoelasticity are attenuation and frequency dependent propagation velocity (dispersion) of shear waves. In comparison with sonoelastography, which typically uses vibration frequencies in the 100-500 Hz range, the frequencies of the shear waves excited in the simulations and experiments here are higher, on the order of one to a few kilohertz. Higher and lower frequencies can be generated easily by varying the spatial frequency of the pushing beam. Higher frequency shear waves will be attenuated more rapidly, but because they are generated by acoustic radiation force at the point of interest, they need propagate no more than a few wavelengths to enable a measurement. Therefore, tissue may be examined over a range of frequencies where the use of externally generated shear waves would be precluded by attenuation. The application of spatially modulated radiation force as described gives rise to a shear wave with a well defined frequency, and points to a potential to measure the frequency dependence of shear wave speed. In a simple elastic medium, the applied wavelength and measured frequency are linearly related. In a viscoelastic medium where shear velocity is a function of frequency, we would expect a deviation from this linear behavior. By applying a sequence of spatially modulated pushing pulses over a range of spatial frequencies and measuring the induced frequency the wave speed at the observed frequency may be estimated.

In conclusion, a method for the calculation of shear modulus using spatially modulated impulsive acoustic radiation force has been presented. In both the simulations and in vitro experiment we find good agreement between the modulus estimated by spatially modulated radiation force and ground truth or MTS measurements. The advantage of the proposed technique compared with other methods is the relative ease with which vibration frequency may be estimated within tissue, compared to the difficult problem of estimating shear wavelength in tissue. The proposed method requires at most high-pass filtering the ultrasonically measured displacement to remove low-frequency motion. In contrast, inversion techniques often require the estimation of second derivatives of displacement with respect to space and time, resulting in a very noise-sensitive estimate.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

I claim:

1. A method for determining a shear modulus of a material having a density, comprising the steps of:
    applying a disturbance having a known spatial frequency and wavelength to the material at an initial point,
    causing a shear wave to be produced in the material;
    detecting the shear wave;
    determining a temporal frequency of the shear wave;
    calculating the shear modulus of the material using the determined temporal frequency, known density of the material, and wavelength of the shear wave; and
    providing the shear modulus value of the material as an output.

2. The method as recited in claim 1, wherein the material comprises human or animal soft tissues.

3. The method as recited in claim 1, further comprising determining temporal frequencies at several points of the material and averaging to determine an average temporal frequency for the step of determining the shear modulus of the material.

4. The method as recited in claim 1, wherein the step of determining the temporal frequency comprises determining the temporal frequency through ultrasonic motion tracking.

5. The method as recited in claim 1, wherein the step of applying the disturbance having the spatial frequency comprises using an acoustic radiation force impulse to generate the disturbance.

6. An apparatus for determining a shear modulus value of a material having a known density, comprising:
    a transducer for generating at least one acoustic radiation impulse toward the material, the at least one acoustic radiation impulse having known spatial frequency and wavelength to produce a shear wave propagating in the material;
    a detecting device for detecting the shear wave and detecting a temporal frequency of the shear wave;
    a calculating device for calculating the shear modulus value the material using the detected temporal frequency, known density of the material, and known wavelength of the shear wave; and
    an output coupled to the calculating device for indicating the shear modulus value of the material.

7. An apparatus as disclosed in claim 6, wherein the calculating device determines temporal frequencies at several points of the material and averages to determine an average temporal frequency.

8. An apparatus as disclosed in claim 6, wherein the detecting device detects the temporal frequency through ultrasonic motion tracking.

* * * * *